United States Patent [19]

Crowninshield et al.

[11] Patent Number: 5,066,304
[45] Date of Patent: Nov. 19, 1991

[54] PROSTHETIC INTERPOSITIONAL DEVICE/COUPLER

[75] Inventors: Roy D. Crowninshield, Warsaw; Roy Y. Hori, both of Warsaw, Ind.

[73] Assignee: Zimmer, Inc., Warsaw, Ind.

[21] Appl. No.: 649,094

[22] Filed: Feb. 1, 1991

Related U.S. Application Data

[62] Division of Ser. No. 325,799, Mar. 20, 1989, Pat. No. 5,015,257.

[51] Int. Cl.$^5$ ............................................. A61F 2/32
[52] U.S. Cl. .................................................... 623/22
[58] Field of Search ...................... 623/16, 18, 20, 22, 623/23

[56] References Cited

U.S. PATENT DOCUMENTS 4,921,500  5/1990  Averill et al. .......................... 623/18
4,995,883  2/1991  Demane et al. ........................ 623/23

FOREIGN PATENT DOCUMENTS 382429  8/1990  European Pat. Off. .

OTHER PUBLICATIONS

Richards, "Orthopaedic Price List", No. 62-8586, Apr. 15, 1987.

*Primary Examiner*—David J. Isabella
*Attorney, Agent, or Firm*—Margaret L. Geringer

[57] ABSTRACT

The present invention relates to a prosthetic interpositional device/coupler designed to be interposed between the neck and head of a femoral prosthesis. One example of a contemplated environment of use of the inventive interpositional device/coupler is in the situation where the prosthesis has a neck of one material and a head of another material. The inventive interpositional device/coupler may be made with an outer wall having a taper designed to match the taper of the head and with an inner wall having a taper designed to match the taper of the neck. These tapers may differ. Additionally, the inner and outer surfaces may have different surface textures from one another so as to make the respective walls compatible with the surface texture of the material of which the adjacent structure, head or neck, is made. Three embodiments of the inventive interpositional device/coupler are disclosed. The third embodiment is similar to the second embodiment except that the end wall is much thicker than the end wall in the second embodiment so that the device is greater in length than the second embodiment. The first embodiment does not include an end wall and may be shorter in length than either the second or third embodiment.

3 Claims, 2 Drawing Sheets

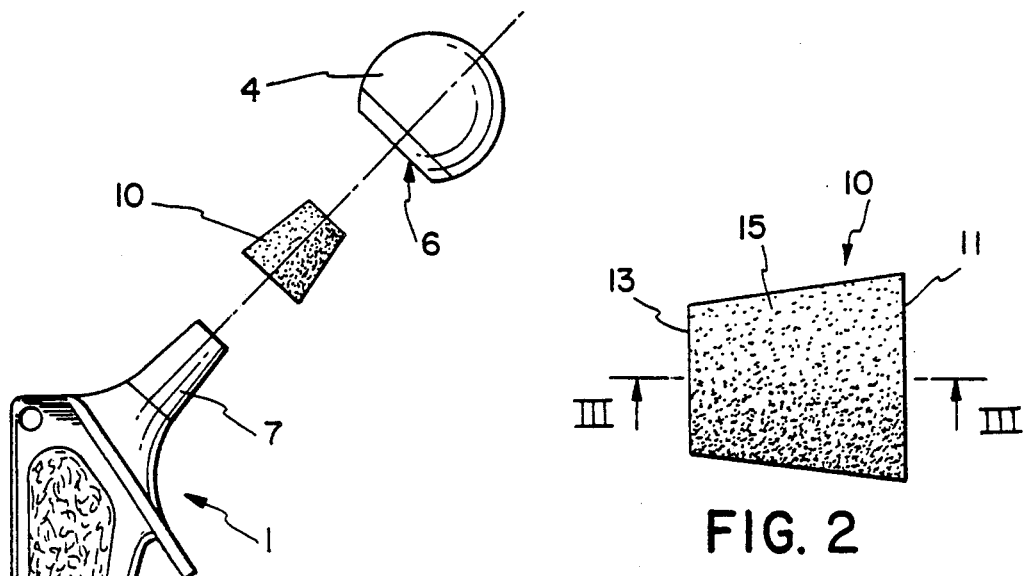
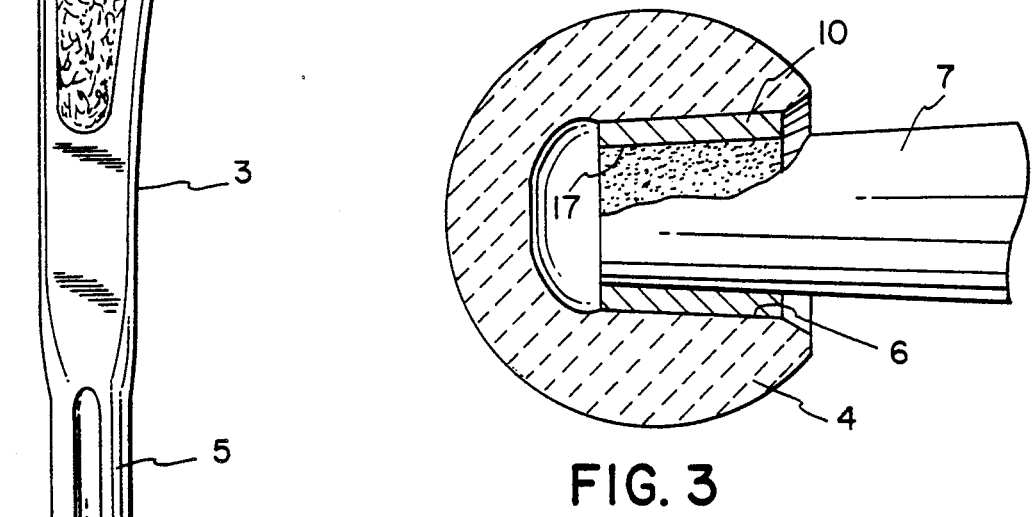
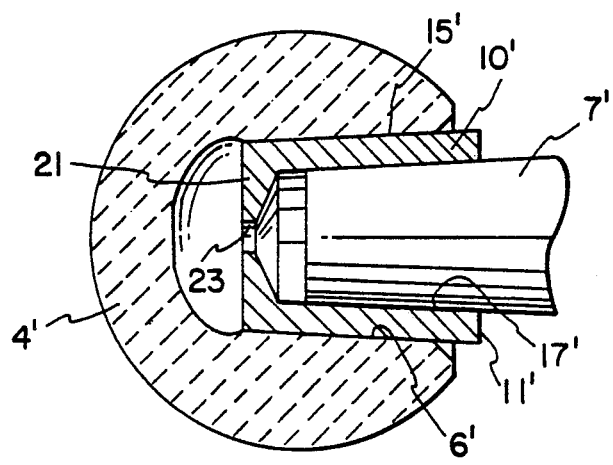

PROSTHETIC INTERPOSITIONAL DEVICE/COUPLER

This is a division of application Ser. No. 07/325,799, filed Mar. 20, 1989, now U.S. Pat. No. 5,015,257.

BACKGROUND OF THE INVENTION

The present invention relates to a prosthetic interpositional device/coupler. In the prior art, it is generally known to interpose some structure between the head and neck of a prosthesis for various reasons. However, Applicant is unaware of any such device having structure like that of the present invention, nor for the specific purposes thereof.

The following prior art is known to applicant:

U.S. Pat. No. 4,005,495 to Locke et al. discloses a ceramic cap bone prosthesis and method of implantation. The invention consists of a cap 1 designed to be mountable over a neck 2 which comprises the femoral head of the existing bone which has been surgically shaped to receive the cap 1. A thrust plate 4 is mounted on the bone 10 through an opening formed therein, with the thrust plate 4 being used to assist in locking the cap 1 on the neck 2. The present invention differs from Locke et al., among other reasons, as including embodiments of an interpositional device/coupler which annularly engages the cap as well as the neck of a prosthesis rather than of living bone tissue.

U.S. Pat. No. 4,173,797 to Langlais et al. discloses a prosthesis for arthroplasty of the hip which includes a thin metal cup 16 having a lateral skirt member 18 which cup 16 is designed to be mountable over the head 22 of the existing femur 1 with this head 22 having been machined to conform to the configuration of the cup 16. Again, this is different from the teachings of the present invention, since the inventive interpositional device/coupler is designed to be interposed between a cap and neck of a prosthesis.

U.S. Pat. No. 4,227,265 to Frey discloses a bone implant with plastic insert between elements of different mechanical properties. The plastic insert consists of a cap-like sleeve 4 designed to be mountable over the neck of a stem 1 and to engage, with its outer surfaces, the inner surfaces of a cavity formed in the head 2. A screw 3 is used to secure the head 2 to the stem 1. The present invention is different from the teachings of Frey, among other reasons, as requiring the interpositional device/coupler to be made of metal, as allowing the inner and outer surfaces of the interpositional device/coupler to subtend differing angles and as allowing the inner and outer surfaces thereof to have differing surface textures.

U.S. Pat. No. 4,676,797 to Anapliotis et al. discloses a unit for a resection prosthesis consisting of a prosthesis made up of a plurality of sections including, for example, an intermediate member 5 designed to couple together a head member 1 and a further intermediate member 9. The present invention is clearly distinct from the teachings of this patent, among other reasons, as including an interpositional device/coupler designed to be directly interposed between the head and neck of the prosthesis.

U.S. Pat. No. 4,687,488 to Frey discloses a femur head prosthesis including a joint head 5 having a sleeve welded thereto by means of a weld 12. This is different from the teachings of the present invention wherein the head includes pre-existing inner surfaces which are engaged by an insertable interpositional device/coupler into which may be inserted the neck of the prosthesis. Other distinctions exist.

European Patent Application No. 144,209 to Weightman, et al. discloses an endoprosthetic bone joint component device which includes a plastic part 30 designed to be interposed between the neck 12 of a prosthesis and the head 20 thereof, with the head 20 preferably being made of ceramic and with the neck 12 preferably being made of metal. The present invention differs from the teachings of this European Patent Application, among other reasons, as providing a metallic interpositional device/coupler having inner and outer surfaces which may subtend differing angles, with these inner and outer surfaces also preferably having differing surface textures.

European Patent Application No. 193,681 to Elloy discloses joint prostheses including a plastic sleeve 7 or 13 designed to be interposed between a head and neck of a prosthesis. The present invention differs from the teachings of Elloy for the same reasons set forth hereinabove concerning U.S. Pat. No. 4,227,265 to Frey and European Patent Application No. 144,209 to Weightman, et al.

European Patent Application No. 202,141 to Flegeau, et al. discloses a femoral head for a hip joint prosthesis including a head with a sleeve device mounted thereto. The sleeve device has a supporting ledge 13 for the head 11. The present invention differs from the teachings of Flegeau, et al. for reasons including the differing textures of the inner and outer surfaces thereof.

German Auslegeschrift 25 24 923 to Frey discloses a hip joint prosthesis including a metallic sleeve 3 interposed between the stem 5 and the head 1 thereof. The present invention differs from the teachings of Frey for reasons including the differing surface textures of the inner and outer surfaces of the sleeve of the present invention.

German Offenlegungsschrift 26 18 763 to Ribonet, et al. discloses a joint prosthesis including a head 1 mounted to a stem 6 via a sleeve 4 designed to be soldered to the stem 6 to prevent relative translational motion. The present invention differs from this teaching for reasons including the fact that the inventive interpositional device/coupler is frictionally engaged to the neck of the prosthesis without soldering, and, additionally, due to the differing surface textures of the inner and outer surfaces.

SUMMARY OF THE INVENTION

The present invention includes the following interrelated aspects and features:

a) the inventive interpositional device/coupler is disclosed in three preferred embodiments thereof. In a first embodiment, the device consists of a tapered sleeve having inner and outer surfaces and open ends. Second and third embodiments are similar to the first embodiment, but have one end with an end wall having a small opening therethrough.

b) In each of the embodiments of the present invention, the inventive interpositional device/coupler is designed to be made of metal. One preferred material for the interpositional device/coupler is a titanium alloy known as TIVANIUM® Ti-6A1-4V Alloy. "TIVANIUM" is a registered trademark of Zimmer, Inc.

c) The preferred environment of use of the inventive interpositional device/coupler is as an interface between a prosthetic head of one material and a prosthetic neck of a diverse material from the material of the head. The interpositional device/coupler is carefully designed for each particular use so as to be compatible with the head and neck between which it is to be associated. In this regard, the taper of the outer wall of the interpositional device/coupler is preferably made to be compatible with the taper of the internal cavity of the head in which the interpositional device/coupler is to be installed. Similarly, the taper of the inner surface of the interpositional device/coupler is designed to be compatible with the taper of the outer surface of the neck which is to be inserted therein. These tapers may differ from one another in particular applications.

d) In a further aspect, in the preferred embodiment of the present invention, the surfaces of the respective inner and outer surfaces of the interpositional device/coupler are specifically made to render them best compatible with the surface of the material which is to be engaged therewith. Thus, in a situation where the outer surface of the interpositional device/coupler is to engage inner surfaces of a prosthetic head made of a ceramic material, the surface texture of the outer wall of the interpositional device/coupler may be made relatively rough. One example of a degree of roughness which would be suitable for this purpose is defined as a surface finish of 116.7 micro inch arithmetic average. Continuing with this example, it might also be the case that the inner surface of the interpositional device/coupler is intended to engage the outer surfaces of a metallic neck. In such case, the inner surface of the interpositional device/coupler may be finished with a surface texture relatively less rough than the degree of roughness of the surface texture of the outer surface of the interpositional device/coupler described above. An example of a degree of roughness of the inner surface of the interpositional device coupler which would be suitable in this example is defined as a surface finish of 32 micro inch arithmetic average.

e) The inner and outer surfaces of the interpositional device/coupler are intended to be used to mount a prosthetic head to a prosthetic neck solely through frictional interaction therebetween. The respective surface textures of the inner and outer surfaces are specifically designed to best facilitate frictional gripping of the respective neck and head of the prosthesis between which the inventive interpositional device/coupler is to be interposed.

f) In a further aspect, the inventive interpositional device/coupler may be used in a modular system wherein the interpositional device/coupler allows mating together of diverse prosthetic heads and stems.

Accordingly, it is a first object of the present invention to provide an improved prosthetic interpositional device/coupler.

It is a further object of the present invention to provide such an improved prosthetic interpositional device/coupler which may be frictionally inter-engaged between a head and neck of a prosthesis.

It is a yet further object of the present invention to provide an improved prosthetic interpositional device/coupler with inner and outer surfaces of differing tapers and surface textures.

It is a still further object of the present invention to provide an improved prosthetic interpositional device/coupler which is intended to be interposed between a head of one material and a neck of another material.

These and other objects, aspects and features of the present invention will be better understood from the following detailed description of the preferred embodiments, when read in conjunction with the appended drawing figures.

BRIEF DESCRIPTION OF THE DRAWINGS

FIG. 1 shows an exploded view of a prosthesis having one embodiment of the present invention incorporated therewith.

FIG. 2 shows an enlarged side view of a first embodiment of the inventive interpositional device/coupler.

FIG. 3 shows a cross-sectional view of the sleeve, along with cross-sectional views of the head and neck between which the sleeve is interposed, along the line III—III of FIG. 2.

FIG. 4 shows a cross-sectional view of a second embodiment of the interpositional device/coupler along with views of the head and neck between which the interpositional device/coupler is interposed.

SPECIFIC DESCRIPTION OF THE PREFERRED EMBODIMENTS

Figure 5:
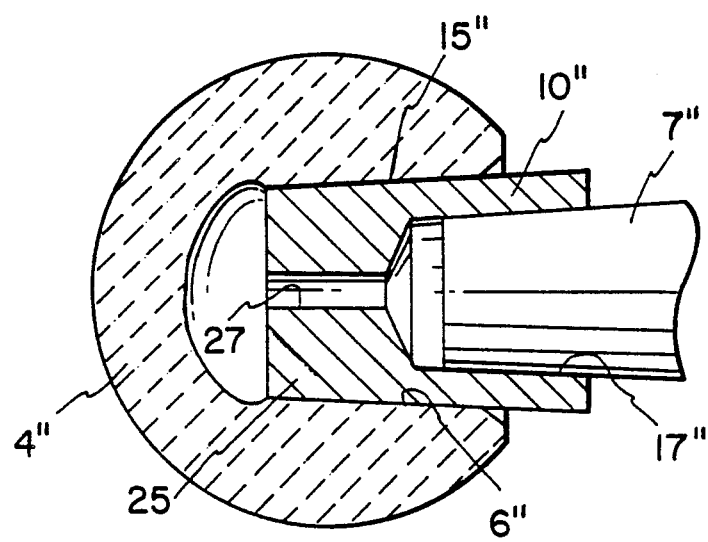
FIG. 5 shows a cross-sectional view of a third embodiment of the interpositional device/coupler along with views of the head and neck between which the interpositional device/coupler is interposed.

With reference, first, to FIG. 1, a femoral prosthesis is generally designated by the reference numeral 1 and is seen to include a first component 3 having a stem 5 and a neck 7 on one end of the stem 5. Further, the prosthesis 1 includes a head 4 with a blind bore on one side thereof.

In the example shown in FIG. 1, interposed between the head 4 and neck 7 of the prosthesis 1 is a interpositional device/coupler 10. In the FIG. 1 showing, the interpositional device/coupler 10 is but one embodiment of the plurality of embodiments of interpositional device/coupler disclosed herein. The particular interpositional device/coupler shown in FIG. 1 is seen in greater detail in FIGS. 2 and 3.

With reference to FIGS. 2 and 3, it is apparent that the interpositional device/coupler 10 includes a first end 11, a second end 13, an outer surface 15 and an inner surface 17. FIG. 3 shows the inventive interpositional device/coupler 10 interposed between the neck 7 and head 4 of the prosthesis 1 better shown in FIG. 1.

Often, as explained hereinabove, a prosthesis will consist of a stem/neck of one material and a head of a diverse material. In particular, while titanium alloys have been found to be advantageous materials for use in stem/neck constructions due to compatibility with living bone tissue, to the contrary, it has been found that ceramic materials may be advantageous over metallic materials, including titanium alloys for use in manufacturing the head portion of a prosthesis. Among other reasons, this is due to the fact that the head portion of a prosthesis acts as a bearing and ceramic materials have been found to be very beneficial for this purpose.

As is also known, the surface texture of a ceramic body may differ from the surface texture of a metallic body and, as such, it is important to take this fact into consideration in designing a prosthesis. As seen in FIGS. 2 and 3, in the preferred embodiment of the interpositional device/coupler 10, the surface texture of the outer surface 15 is coarser than the surface texture of the inner surface 17. In one preferred embodiment of the inventive interpositional device/coupler 10, the surface texture of the outer surface 15 of the interpositional device/coupler 10 may be 116.7 micro inch arithmetic average, whereas the surface texture of the inner surface 17 may be 32 micro inch arithmetic average. Of course, these degrees of coarseness are merely examples of degrees of coarseness which may be chosen for the surfaces 15, 17 of the coupler 10.

As should be understood, the relatively high degree of coarseness of the outer wall 15 of the interpositional device/coupler 10 is provided to result in a better frictional engagement and retention with the inner surfaces of the cavity 6 of the ceramic head 4. In a similar manner, the relatively lesser coarseness of the inner surfaces 17 of the interpositional device/coupler 10 are particularly suitable for frictional engagement and retention of the metallic neck 7.

In a further aspect, often the angle of taper of the cavity in the head of a prosthesis may be different from the angle of taper of the neck thereof. Such differences in the degree of taper may result in frictional engagement of the head and neck along a line of contact rather than a surface of contact. Such circumstances reduce the surface area of frictional inter engagement and, thereby, result in a lessening of the ability of the head to be frictionally retained on the neck. In this regard, the outer surface 15 of the interpositional device/coupler 10 is designed with a taper which matches the degree of taper of the blind bore 6, whereas the inner surface 17 of the interpositional device/coupler 10 has a degree of taper which matches the degree of taper of the neck 7. In this way, the interpositional device/coupler 10 causes both the head 4 and neck 7 to be engaged with the interpositional device/coupler 10 in large surface areas of contact which promote frictional retention thereof. For example, the taper of the outer surface 15 may be 5° 44' whereas the taper of the inner surface 17 may be 6°. Other desired diverse degrees of taper may be provided as desired, depending upon the respective degrees of taper of the head blind bore taper and neck taper.

FIGS. 4 and 5, respectively, disclose additional embodiments of interpositional device/coupler devices in accordance with the teachings of the present invention. While these individual embodiments will be described in great detail hereinbelow, it should be understood that these embodiments have several aspects in common with the interpositional device/coupler 10 described hereinabove with reference to FIGS. 1-3. Firstly, each of the interpositional device/coupler devices of FIGS. 4 and 5 includes the relationship described with respect to FIGS. 1-3 concerning the degrees of coarseness of the inner and outer surfaces of the interpositional device/coupler. Furthermore, the interpositional device/coupler devices of FIGS. 4 and 5 share with the interpositional device/coupler 10 the relationships between the angles of taper of the inner and outer surfaces thereof, so as to match the respective tapers of the stem and head of the associated prosthesis.

Now, with reference to FIG. 4, a second embodiment of interpositional device/coupler is designated by the reference numeral 10' and like elements are designated with like primed reference numerals. Of note in FIG. 4, are the stem 7' and the head 4' having a blind bore 6'.

The interpositional device/coupler 10' includes a first end 11', a second end having a wall 21 closed except for a small central opening 23, an outer surface 15' and an inner surface 17'. The interpositional device/coupler 10' may have a greater length than interpositional device/coupler 10.

The opening 23 is provided in the interpositional device/coupler 10' so that as the stem 7' is mounted within the interpositional device/coupler 10', any air or other material which might otherwise be trapped between the end of a stem 7' and the inner surfaces of the wall 21 may be expelled therefrom to allow a secure fit. Furthermore, the opening 23 may be used in conjunction with a tool (not shown) in assembling or disassembling the interpositional device/coupler 10' with respect to the neck 7' and head 4'.

With reference to FIG. 5, where like elements from FIGS. 1-4 are designated with like double primed reference numerals, the interpositional device/coupler 10" is seen in association between the neck 7" and the head 4" of prosthesis 1". The interpositional device/coupler 10" includes an outer surface 15", an inner surface 17", as well as a first and 11", and a second end consisting of a wall 25 extending across the interpositional device/coupler 10", except for an opening 27 extending therethrough.

The interpositional device/coupler 10" is similar to the interpositional device/coupler 10' with the main difference being the fact that the interpositional device/coupler 10" has a wall 25 much thicker than the wall 21 of the interpositional device/coupler 10'. The extra degree of thickness of the wall 25 of the interpositional device/coupler 10" is provided to lengthen the interpositional device/coupler 10". The opening 27 through the wall 25 of the interpositional device/coupler 10" is provided for the same purpose as the corresponding opening 23 of the interpositional device/coupler 10'. It is emphasized that in the preferred embodiments of the present invention the interpositional device/coupler 10' is greater in length than the interpositional device/coupler 10, and is shorter in length than the interpositional device/coupler 10". These differing lengths are provided to enhance versatility.

In assembling a prosthesis together, wherein one of the embodiments of the interpositional device/coupler 10, 10' or 10" is to be employed, the interpositional device/coupler may first be inserted in the head of the prosthesis or, alternatively, may first be assembled over the neck of the prosthesis. In either case, the interpositional device/coupler is forced onto the adjacent structure in such a manner that frictional engagement acts to retain the interpositional device/coupler in assembled relation on the adjacent components. Through use of an interpositional device/coupler device in accordance with the teachings of the present invention, a more secure assembly of a prosthetic head to the corresponding prosthetic stem/neck may be had, especially in circumstances where these diverse components are made of diverse materials. The interpositional device/coupler of the present invention acts as an interface between these components, providing the desired degree of surface roughness and wall taper for each component which best facilitates assembly of the components together in a secure fashion.

Of course, it should be understood that the inventive interpositional device/coupler embodiments may be used in a modular system of prosthetic heads and stems of varying sizes or varying prosthesis designs.

Accordingly, embodiments of an interpositional device/coupler have been disclosed which fulfill each and every one of the objects of the invention as set forth hereinabove, and which provide a device which fulfills a need not taught in the prior art in a manner improving the quality, fit and retention of prosthetic components.

Of course, various changes, modifications and alterations of the teachings of the present invention may be contemplated by those skilled in the art without departing from the intended spirit and scope of the present invention. As such, it is intended that the present invention only be limited by the terms of the appended claims.

We claim:

1. A set of implant components comprising a plurality of couplers wherein the plurality of couplers are available in a plurality of differing lengths to enable the desired length coupler to be selected for interpositioned engagement between a femoral prosthesis head and a neck of a femoral prosthesis stem to provide a desired distance therebetween, and wherein each coupler comprises a hollow sleeve having a first end and a second end and wherein the first end of each coupler in the set is open for fitting over the neck of the femoral stem, and wherein the second end of at least one of the couplers in the set includes an end wall generally transverse to a longitudinal axis of said coupler and wherein the second end of at least one other of the couplers is open without any end wall, and wherein said at least one of the couplers including said end wall has a greater length than said at least one other of the couplers having the open second end, and wherein all couplers in the set having an open second end are shorter than any couplers in the set in which the second end includes an end wall.

2. The set of implant components of claim 1, wherein said coupler generally tapers inwardly from said first end to said second end.

3. The set of implant components of claim 1, wherein said end wall has a small opening therethrough.

* * * * *